(12) United States Patent
Welle et al.

(10) Patent No.: US 6,187,768 B1
(45) Date of Patent: Feb. 13, 2001

(54) KIT FOR FLUSHING MEDICAL DEVICES AND METHOD OF PREPARATION

(75) Inventors: Charles J. Welle; Steven C. Felton; Mohammad A. Khan, all of Sandy, UT (US)

(73) Assignee: Becton, Dickinson and Company, Franklin Lakes, NJ (US)

( * ) Notice: Under 35 U.S.C. 154(b), the term of this patent shall be extended for 0 days.

(21) Appl. No.: 09/323,984

(22) Filed: Jun. 1, 1999

(51) Int. Cl.$^7$ .......................... A61K 31/43; A61K 31/65; A61K 31/70; A61K 31/545; A61K 31/18
(52) U.S. Cl. .......................... 514/199; 514/152; 514/24; 514/25; 514/29; 514/200; 514/601
(58) Field of Search .................................. 514/199, 152, 514/24, 25, 29, 200, 601

(56) References Cited

U.S. PATENT DOCUMENTS

| | | | |
|---|---|---|---|
| 3,987,797 | 10/1976 | Stephenson | 128/335.5 |
| 4,128,173 | 12/1978 | Lazarus et al. | 206/570 |
| 4,465,666 | 8/1984 | Lukas et al. | 424/145 |
| 4,713,402 | 12/1987 | Solomon | 523/112 |
| 4,919,889 | 4/1990 | Jones et al. | 422/40 |
| 4,950,256 | 8/1990 | Luther et al. | 604/265 |
| 4,980,163 | 12/1990 | Blackburn et al. | 434/94.63 |
| 4,999,210 | 3/1991 | Solomon et al. | 427/2 |
| 5,019,096 | 5/1991 | Fox, Jr. et al. | 623/1 |
| 5,041,100 | 8/1991 | Rowland et al. | 604/265 |
| 5,362,754 | 11/1994 | Raad et al. | 514/566 |
| 5,688,516 | 11/1997 | Raad et al. | 424/409 |

FOREIGN PATENT DOCUMENTS

| | | | |
|---|---|---|---|
| 2 749 169 | 12/1997 | (FR) | A61K/9/08 |

OTHER PUBLICATIONS

A. D. Russell, Inhibition and Destruction of the Microbial Cell, *EDTA–Drug Combinations*, p. 209–224 (1971).
Wooley et al., "In Vitro Action of Combinations of Antimicrobial Agents and EDTA–Tromethamine on *Escherichia coli*", Am J. Vet Res, 44(6):1154–58 (1982).
*The Merck Index*, 11th Edition. Merck & Co., Inc. Publishers pp 550, 606, 735, 738, 745 and 1035 (1989).
*Remington's Pharmaceutical Sciences*, 18th Edition. Alfonso R. Gennaro, Editor, Mack Publishing Company, Easton PA. 1314 (1990).
A. D. Russell, Inhibition and Destruction of the Microbial Cell, *EDTA–Drug Combinations*, p. 209–244 (1971).
Wooley et al., "In Vitro Action of Combinations of Antimicrobial Agents and EDTA–Tromethamine on *Escherichia coli*", Am J. Vet Res, 44(6):1154–58 (1982).
Wooley et al., "The Vitro Action of Combinations of Antimicrobial Agents and EDTA–Tromethamine on *Pseudomonas Aeruginosa*", Am J. Vet Res, 44(8):1521–24 (1982).
Tyler et al., *Pharmacognosy*, Eighth Edition, p. 367–371 (1981).
Susan Budavari, Editor, *The Merck Index; An Encyclopedia of Chemical, Drugs and Biologicals*. Twelfth Edition p. 1061 (1996).
Wiernikowski et al., "Bacterial Colonization of Tunneled Right Atrial Catheters in Pediatric Oncology: A Comparison of Sterile Saline and Bacteriostatic Saline Flush Solutions", Am J. Pediatr Hematol Oncol. 13(2):137–140 (1991).
Schwartz et al., "Prevention of Bacteremia Attributed to Luminal Colonization of tunneled Central Venous Catheters With Vancomycin–Susceptible Organisms", *Journal of Clinical Oncology*. 8(9):1591–1597 (1990).
Kamal et al., "Reduced Intravascular Catheter Infection by Antibiotic Bonding", *JAMA*, May 8, 1991, 265(18):2364–68 (1991).
Mandel et al., *Principles and Practice of Infectious Diseases*, Third Edition, p. 2189–96 (1990).

*Primary Examiner*—Kevin E. Weddington
(74) *Attorney, Agent, or Firm*—Eric M. Lee, Esq.

(57) ABSTRACT

A kit and for flushing a medical device a method of preparing the kit is disclosed. The kit includes a container containing a mixed solution a unit dose of a pharmacologically effective amount of an antimicrobial agent and a second agent. The mixed solution has been mixed in a carrier solution and lyophilized. The second agent is an anticoagulant, an antithrombotic agent or a chelating agent. The kit and method are useful for maintaining the patency of indwelling medical devices such as catheters and for preventing infections caused by bacterial growth in catheters.

18 Claims, 1 Drawing Sheet

KIT FOR FLUSHING MEDICAL DEVICES AND METHOD OF PREPARATION

FIELD OF THE INVENTION

The present invention relates to indwelling medical devices, for example, catheters. More particularly, the present invention relates to kits and methods for preparing these kits which can be used to flush these medical devices to maintain their patency.

BACKGROUND OF THE INVENTION

Indwelling medical devices, including intravascular catheters, are among the most commonly used medical devices. Such catheters are routinely placed into a patient s vascular system for many procedures and often are left in place for extended periods. Since an intravascular catheter is a direct path from the outside environment to the patients bloodstream, the catheter presents a substantial and continuous potential for introduction of microorganisms into the patient's bloodstream. Clinicians have developed many protocols related to placement, use, attachment and detachment of fluid handling devices and other procedures related to catheters. The goal of almost all of these procedures is to avoid introduction of a microorganism into the patient's bloodstream.

When a medicament is introduced into a patient through a catheter, the practitioner commonly follows the introduction with a flush solution that may include an anticoagulant such as heparin. The purpose of the flush solution is to move the medicament out of the catheter so that the entire dosage is delivered, and to leave a residual fill in the catheter so that the patient's blood does not back up in the catheter and possibly form a clot that would occlude the bore of the catheter. Thus, when the catheter is subsequently needed again, the properly flushed catheter is likely fully patent and ready for the next usage.

In 1988, Root, et al., published a study that reported on the effect of disodium ethylene diamine tetra acetic acid (EDTA), a compound well known for its chelating properties in vivo and widely used as an anticoagulant in vitro. The authors compared EDTA, heparin and vancomycin/heparin for effectiveness upon the growth of S. epidermis in vitro and its relation to infection prophylaxis of Hickman catheters in their report in *Antimicrob. Agents Chemother.*, 32:1627–1631, (1988). Recently, Raad, et al., in U.S. Pat. No. 5,363,754, disclosed that pharmaceutical compositions of a mixture of minocycline and EDTA were useful in maintaining the patency of a catheter port. The compositions are useful in preventing adhesions of infectious organisms, such as S. epidermidis and S. aureus. More recently, Raad, et al. in U.S. Pat. No. 5,688,516, further disclosed that effective catheter flush solutions could he prepared with non-glycopeptide antimicrobial agents other than vancomycin and a second agent selected from the group consisting of (a) an anticoagulant, (b) an antithrombotic agent, and (c) a chelating agent. Raad, et al. teaches that since many antibiotic agents are not particularly stable at ambient conditions in aqueous solutions, the disclosed compositions are stable and effective for about one month when stored under refrigerated conditions. In addition, the solution should be brought to room temperature before administration to a patient. Alternatively, Raad, et al. teaches a kit including three compartments, the compartments containing the antimicrobial agent, the chelating, anticoagulant or antithrombotic agent and a diluent such as saline, Ringers solution or water so that the clinician could mix the components prior to administration to the patient, thereby avoiding the reported stability problems.

U.S. patent application Ser. No. 09/160,745, filed on Sep. 25, 1998 and entitled Catheter Flush Solution, discloses solutions useful for flushing intravascular catheters comprising a pharmacologically acceptable sodium salt, a pharmacologically acceptable calcium salt, a pharmacologically acceptable potassium salt, and about one milligram per milliliter of polyhexamethylene biguanide in an aqueous admixture. Examples of pharmacalogically acceptable salts disclosed therein include sodium chloride, calcium chloride and potassium chloride.

While the disclosures of Raad, et al. and U.S. application Ser. No. 09/160,745 teach a variety of antimicrobial agents combined with a variety of other compounds, such solutions typically have a short shelf-life once the components are mixed together, particularly solutions of minocycline and EDTA (hereinafter referred to as M-EDTA). A mixed solution of M-EDTA turns yellow when stored and has a shelf-life of less than seven days, and M-EDTA solutions must be used within three days of mixing.

One method of solving the problem with the short shelf-life of the mixed solutions is to provide assembled kits containing a vial of EDTA, a vial of minocycline, and a device for delivering the mixed solutions to a catheter, such as a syringe. Another method of addressing the problem is for the hospital pharmacy to prepare the solution upon request as required. However, both of these methods are expensive and cost prohibitive in practice. One particular problem associated with both of these methods is that there is typically excess solution that must be discarded.

There is an explicit need for a kit and a method for providing catheter flush solutions that have a long shelf life and are simple and inexpensive to use in the hospital setting. It would be useful to provide a kit containing a unit dose of the solution containing all of the components (e.g., an antimicrobial agent and an anticoagulant) which is ready to be mixed with a carrier solution and flushed through an indwelling medical device such as a catheter.

SUMMARY OF INVENTION

Accordingly, the present invention generally provides a kit and a method for preparing a kit for flushing a medical device, such as a catheter. The kit includes a container containing a dry mixture of a unit dose of a pharmacologically effective amount of an antimicrobial agent and a second agent selected from the group consisting of an anticoagulant, an antithrombotic agent and a chelating agent. As used herein, pharmacologically effective amount means that the solution is effective in the local area of the medical device. According to the present invention, the dry mixture has been mixed in a carrier solution and lyophilized. In another aspect of the invention, the kit may further include a second carrier solution for reconstituting the lyophilized unit dose.

According to one aspect of the invention, the antimicrobial agent is selected from the group consisting of aminoglycoside, amphothericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, sulfonamide, tetracycline, trimethoprim, a pharmacologically acceptable calcium salt, and a pharmacologically acceptable potassium salt. In another aspect of the invention, the chelating agent is selected from the group consisting of EGTA, diethylenetriamine penta acetic acid, DMSA, deferoxamine, dimercaprol, zinc citrate, a combination of bismuth and citrate, penicillamine, succimer and etidronate. In still another aspect, the anticoagulant is selected from the group consisting of EDTA, heparin, and hirudin.

In a preferred embodiment, the antimicrobial agent is a tetracycline antibiotic, and more preferably, the antimicrobial agent is minocycline. Preferably, the kit contains a unit dose of a pharmacologically effective amount of minocycline and EDTA mixed in a carrier solution and lyophilized. More preferably, the kit includes a preselected amount of a second carrier solution such that when the second carrier solution is mixed with the lyophilized unit dose, the concentration of minocycline is 3 mg/ml and the concentration of EDTA is 30 mg/ml.

Another aspect of the invention involves a method of preparing a solution, which can be used in a kit for flushing a catheter. The method involves mixing in a carrier solution an antimicrobial agent and a second agent selected from the group consisting of an anticoagulant, an antithrombotic agent and a chelating agent. The solution is then lyophilized to provide a unit dose of the mixture which can be reconstituted in a second carrier solution. One exemplary embodiment involves first providing a mixed solution of a pharmacologically effective amount of minocycline and EDTA in a carrier solution, and then lyophilizing the mixed solution. After the mixed solution has been lyophilized, the solution is stored in a container and reconstituted in a liquid. The reconstituted solution can then be flushed through an indwelling medical device, such as a catheter.

Several important advantages will be appreciated from the foregoing summary. One advantage is that the present invention provides a relatively easy and inexpensive unit dose of a flush solution containing all of the flushing solution components lyophilized in a form that is ready to mix and use to flush an indwelling device such as a catheter. The lyophilized solution is easy to package and has a shelf life exceeding at least 6 months, preferably 2 years. Additional features and advantages of the invention will be set forth in the description which follows. It is to be understood that both the foregoing general description and the following detailed description are exemplary and explanatory and are intended to provide further explanation of the invention as claimed.

DETAILED DESCRIPTION

Figure 1:
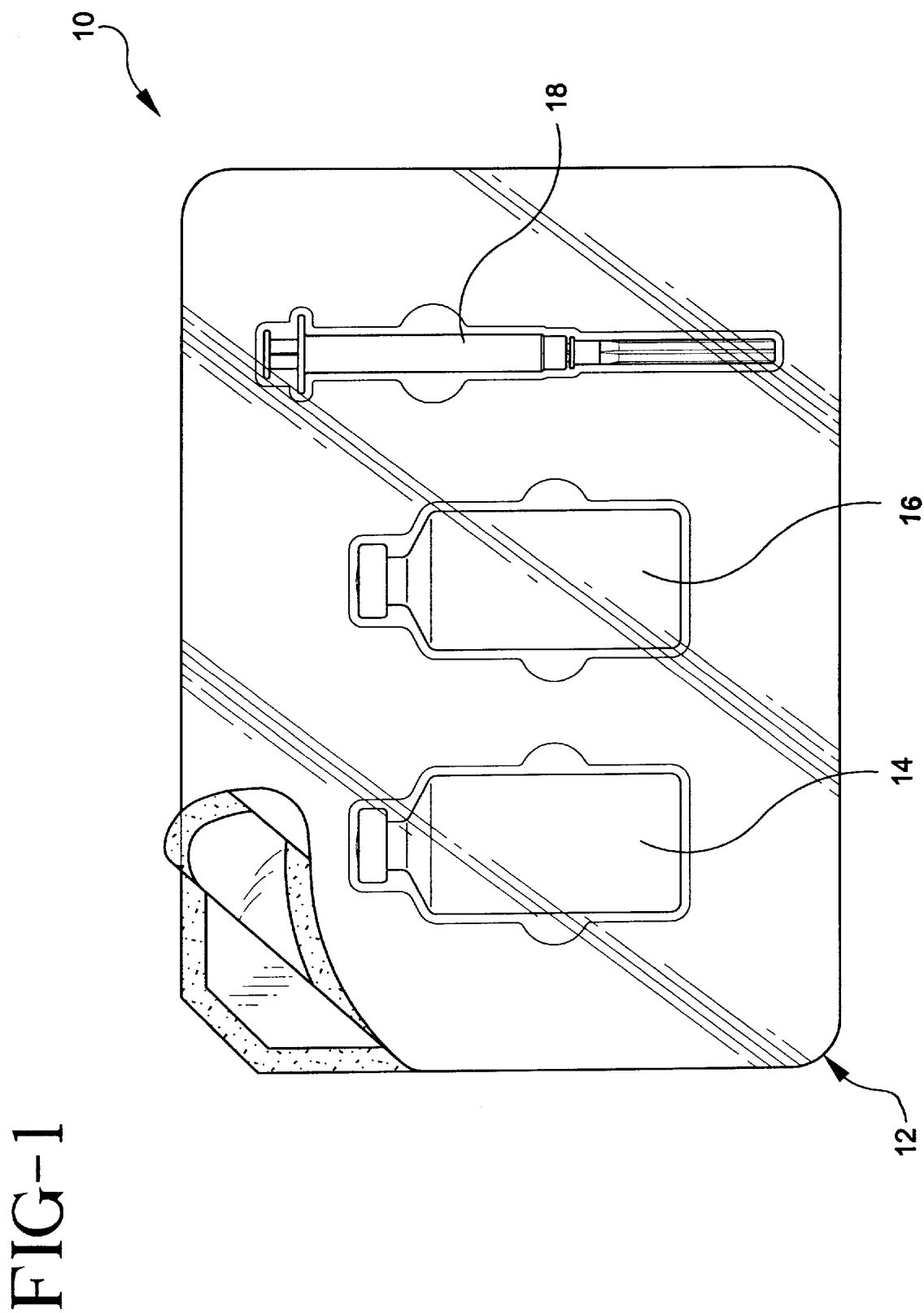
FIG. 1 shows an exemplary kit of the present invention.

As shown generally in FIG. 1, the kit 10 of the present invention includes a package 12 for holding the kit. The kit 10 includes a container 14, such as a vial, containing a dry mixture of a unit dose of a pharmacologically effective amount of an antimicrobial agent and a second agent selected from the group consisting of an anticoagulant, an antithrombotic agent and a chelating agent. According to the invention, the mixed solution has been combined in a carrier solution and lyophilized using lyophilization techniques known in the art. Thus, the lyophilized solid contains includes at least an antimicrobial agent and one of the following: an anticoagulant, an antithrombotic agent or a chelating agent. Preferably, the kit contains a second carrier solution in a second container 16, such as a vial, for reconstituting the lyophilized unit dose. The carrier solution in which the original solution has been lyophilized and the second carrier solution for reconstituting the lyophilized solution include pharmacologically acceptable carrier solutions such as water, Ringers solution or saline.

In a preferred embodiment, the antimicrobial agent is a tetracycline antibiotic, and more preferably, minocycline. In a most preferred embodiment, the kit includes a unit dose of a pharmacalogically effective amount of minocycline is mixed with EDTA in a carrier solution and lyophilized into a powder. Preferably, the kit also includes a preselected amount of a second carrier solution such that when the preselected amount of the second carrier solution is mixed with the lyophilized unit dose, the concentration of minocycline is 3 mg/ml and the concentration of EDTA is 30 mg/ml. For example, a kit could contain 3 ml of the second carrier solution, and thus the unit dose contains at least about 9 mg of minocycline and at least about 90 mg of EDTA.

In another embodiment, the kit includes a container for mixing the lyophilized unit dose with the second carrier solution to reconstitute the unit dose, and a device for delivering the reconstituted unit dose in solution to the medical device. An exemplary device for delivering the reconstituted unit dose is a syringe 18. However, other suitable devices for delivering the reconstituted solution to the medical device are within the scope of this invention. Such delivery devices can include a container with a connection for connecting to the catheter and a drip feeding or pump feeding mechanism. In one embodiment, the syringe can be pre-filled with the second carrier solution, and the reconstituted unit dose can be mixed in the syringe and delivered to the medical device directly from the syringe after mixing.

It will be understood that the antimicrobial agent in the kit can be other antimicrobial agents, for example, aminoglycoside, amphothericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, sulfonamide, tetracycline, and trimethoprim. Such antimicrobial agents are disclosed in U.S. Pat. No. 5,688,516, which is incorporated by reference herein in its entirety.

The antimicrobial agent can also be a pharmacologically acceptable calcium salt, a pharmacologically acceptable sodium salt, and a pharmacologically acceptable potassium salt. More specifically, the antimicrobial agent can be a salt such as sodium chloride dihydrate, calcium chloride, potassium chloride or like salts. An exemplary solution includes sodium chloride in concentration between about 820 mg to about 900 mg, calcium chloride dihydrate in a concentration between about 30 mg to about 36 mg, potassium chloride in a concentration between about 28.5 to about 31.5 mg and about one milligram of polyhexamethylene biguanide hydrochloride in an aqueous admixture with one hundred milliliters of water for injection U.S.P. The solution may also include sodium lactate between about 290 mg and about 330 mg in the one hundred milliliter aqueous admixture. Such solutions are disclosed in copending U.S. application Ser. No. 09/160,745, filed on Sep. 25, 1998 and entitled Catheter Flush, the contents of which are incorporated by reference in its entirety. It will be understood that the antimicrobial agent may include combinations of the aforementioned antimicrobial agents.

In one embodiment of the invention, the mixed solution includes a chelating agent. A wide variety of chelating agents may be used, but preferably the chelating agent is EGTA, diethylenetriamine penta acetic acid, DMSA, deferoxamine, dimercaprol, zinc citrate, a combination of bismuth and citrate, penicillamine, succimer or etidronate. It will be understood that chelating agents such as EDTA and EGTA can function as both a chelating agent and an anticoagulant because the chelation of divalent calcium by these agents can inhibit clotting. In embodiments where separate anticoagulants are used, preferably the anticoagulant is heparin or hirudin. Other anticoagulants are a combination of citrate and heparin, enoxaparin sodium, coumarin and indanedione derivative, anisindione, warfarin, protamine sulfate, streptokinase, urokinase, anti-thrombin III, and atlephase recombinant anistreplase.

Another aspect of the present invention involves a method for preparing a solution for flushing a medical device. The method includes mixing in a carrier solution an antimicrobial agent and a second agent selected from the group consisting of an anticoagulant, an antithrombotic agent and a chelating agent. The mixture is then lyophilized to provide a solid unit dose of the mixture which can be reconstituted in a second carrier solution. The solid unit dose of the solution is stable for extended periods of time and easy to reconstitute.

The kit and method of the present invention can be used to maintain the patency of a variety of indwelling medical devices such as a central venous catheter, an arterial catheter, a peripheral intravenous catheter, a Swan-Ganz catheter, a hemodialysis catheter, an umbilical catheter, a percutaneous nontunneled silicone catheter, a cuffed tunneled central venous catheter as well as with a subcutaneous central venous port.

Experimentation has shown that lyophilized M-EDTA has at least a 6 month to over 2 year shelf life and is efficacious in eradicating catheter related *S. Maltophilia, S. epidermidis* and *C. albicans*. The experiments indicated that lyophilized M-EDTA was highly efficacious in eradicating these organisms from silicone catheter surfaces in a manner comparable with freshly prepared solutions of M-EDTA. The experiments were conducted according to the procedures set forth in U.S. Pat. No. 5,362,754, in which an in vitro model consisting of Modified Robbin's Devices was used to study the formation of biofilm and colonization of catheter segments of *S. maltophilia, S. epidermidis* and *C. albicans*. The following Examples demonstrate the comparable efficacy of lyophilized M-EDTA with freshly mixed M-EDTA solutions and a control solution.

EXAMPLE 1

Efficacy of Lyophilized, Reconstituted M-EDTA

A solution of M-EDTA was prepared as follows. Following the procedures set forth in the Examples of U.S. Pat. No. 5,362,754, a 60 mg/ml solution of EDTA and a 6 mg/ml solution of minocycline were prepared. The 6mg/ml minocycline and 60 mg/ml EDTA were then mixed in equal volumes to constitute a 3 mg/ml minocycline and 30 mg/ml EDTA solution.

Lyophilized M-EDTA samples were prepared by completely freezing the above solution in 1.0 ml and 3.0 ml vials. The samples were placed in a freeze dryer and lyophilized to complete dryness. The samples were then purged with nitrogen and stored for 3 months at 40° C. The 3.0 ml vials were removed from storage and reconstituted with 3 ml of sterile water.

Catheter segments containing the above microorganisms were separately treated with the freshly prepared M-EDTA solution, the reconstituted, lyophilized M-EDTA solution, and a control (dextrose 5% in water) for 4 and 24 hours. The catheter segments were removed at 4 and 24 hours and quantitatively cultured using the scrape-sonication technique described in Khoury et al., Bacterial biofilms in nature and disease, Dialogues in Pediatric Urology 14:1–8 (1991), which is incorporated herein by reference for this purpose. The experiment was performed at 37° C.

The catheter segments treated with freshly prepared M-EDTA and lyophilized, reconstituted M-EDTA solution showed no growth of bacteria. The segments treated with the control solutions were confluent with growth. This experiment demonstrates that the lyophilized M-EDTA solution that was stored and reconstituted was comparably effective in preventing adherent colonies on catheter segments.

EXAMPLE 2

Stability of Lyophilized, Reconstituted M-EDTA

The 1 ml vials of lyophilized M-EDTA solution prepared in Example 1 were stored at 40° C. Individual 1 ml vials were reconstituted and analyzed at various time intervals by high pressure liquid chromatography (HPLC) for concentration to determine stability over time. Samples were analyzed at 0, 7 and 14 day and 1, 2, 4, 5, and 6 month time intervals. Three 1 ml sample vials were removed at each time interval and allowed to equilibrate to room temperature. Then, 1 ml of deionized water was introduced into the each sample vial to reconstitute the powder in solution. The samples were then transferred to HPLC autosampler vials for analysis.

The concentration of minocycline in the samples reconstituted at various time intervals was calculated based on a linear regression calibration curve. The calibration standards served as the controls at each time point. USP Minocycline, Lot No. H-2, was used to generate the standard curves. The purity of this neat compound is listed on the label as 857 μg minocycline per mg of weight. Therefore, the neat compound was only considered to be 85.7% pure. All measured concentrations of minocycline were corrected by multiplying the calculated values by 0.0857 to obtain the true concentrations.

All samples were assayed for minocycline concentrations by HPLC using a Hewlett Packard 4.6×150 mm analytical column containing C* packing, a UV/Vis detector set at 280 nm and a 14 minute run time. Table 1 reports the mean percent recoveries (+/− % Relative Standard Error.

TABLE I

| Storage Time Actual Days of Storage | | Percent Recovery vs Calibration Curve |
| --- | --- | --- |
| 0 Days | 0 | 107.9 (0.0407) |
| 7 Days | 9 | 93.1 (0.0053) |
| 14 Days | 15 | 103.4 (0.0073) |
| 1 Month | 29 | 104.8 (0.0012) |
| 2 Month | 57 | 100.3 (0.0096) |
| 4 Month | 113 | 104.3 (not available) |
| 5 Month | 148 | 102.5 (0.0070) |
| 6 Month | 184 | 101.4 (0.0027) |

The results in Table I demonstrate that the mean at each time point falls within the limits established by the USP (90 to 120%).

It will be apparent to those skilled in the art that various modifications and variations can be made to the present invention without departing from the spirit or scope of the invention. Thus, it is intended that the present invention cover the modifications and variations of this invention provided they come within the scope of the appended claims and their equivalents.

What is claimed is:

1. A kit for flushing a medical device comprising:
a dry lyophilized unit dose of a pharmacologically effective amount of an antimicrobial agent and a second agent selected from the group consisting of an anticoagulant, an antithrombotic agent and a chelating agent.

2. The kit of claim 1, further comprising a second carrier solution for reconstituting the lyophilized unit dose.

3. The kit of claim 1, wherein the antimicrobial agent is selected from the group consisting of aminoglycoside, amphothericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, sulfonamide, tetracycline, trimethoprim, a pharmacologically acceptable sodium salt, a pharmacologically acceptable calcium salt, and a pharmacologically acceptable potassium salt.

4. The kit of claim 3, wherein the chelating agent is selected from the group consisting of EGTA, diethylenetriamine penta acetic acid, DMSA, deferoxamine, dimercaprol, zinc citrate, a combination of bismuth and citrate, penicillamine, succimer and etidronate.

5. The kit of claim 1, wherein the anticoagulant is selected from the group consisting of EDTA, heparin, and hirudin.

6. The kit of claim 1, wherein the antimicrobial agent is a tetracycline antibiotic.

7. The kit of claim 1, wherein the antimicrobial agent is minocycline.

8. A kit for flushing a medical device comprising a lyophilized unit dose of a pharmacologically effective amount of minocycline and EDTA mixed in a carrier solution.

9. The kit of claim 8, wherein the unit dose contains at least about 9 mg of minocycline and at least about 90 mg of EDTA.

10. The kit of claim 8, further comprising a preselected amount of a second carrier solution such that when the second carrier solution is mixed with the lyophilized unit dose, the concentration of minocycline is 3 mg/ml and the concentration of EDTA is 30 mg/ml.

11. A kit for flushing a catheter comprising:
a lyophilized unit dose of mixture of at least about 9 mg of minocycline and at least about 90 mg of EDTA that has been mixed in a carrier solution;
a second carrier solution for reconstituting the lyophilized unit dose;
a container for mixing the second carrier solution and the lyophilized unit dose; and
means for introducing the mixture of the lyophilized unit dose and the second carrier solution into the catheter.

12. A method of preparing a solution for flushing a catheter comprising:
lyophilizing a mixture of a pharmacologically effective amount of minocycline and EDTA in a carrier solution;
storing the lyophilized mixture in a container; and
reconstituting the lyophilized mixture in a liquid.

13. The method of claim 12, wherein the reconstituted solution contains at least about 3 mg/ml of minocycline and at least about 30 mg/ml EDTA.

14. A method for preparing a lyophilized solution for flushing a medical device comprising:
mixing in a carrier solution an antimicrobial agent and a second agent selected from the group consisting of an anticoagulant, an antithrombotic agent and a chelating agent; and
lyophilizing the mixture to provide a unit dose of the mixture which can be reconstituted in a second carrier solution.

15. The method of claim 14, wherein the antimicrobial agent is selected from the group consisting of aminoglycoside, amphothericin B, ampicillin, carbenicillin, cefazolin, cephalosporin, chloramphenicol, clindamycin, erythromycin, gentamicin, griseofulvin, kanamycin, methicillin, nafcillin, novobiocin, penicillin, polymyxin, rifampin, streptomycin, sulfamethoxazole, fulfonamide, tetracycline, trimethoprim, a pharmacologically acceptable sodium salt, a pharmacologically acceptable calcium salt, and a pharmacologically acceptable potassium salt.

16. The method of claim 15, wherein the chelating agent is selected from the group consisting of EGTA, diethylenetriamine penta acetic acid, DMSA, deferoxamine, dimercaprol, zinc citrate, a combination of bismuth and citrate, penicillamine, succimer and Etidronate.

17. The method of claim 16, wherein the anticoagulant is selected from the group consisting of EDTA, heparin, and hirudin.

18. The method of claim 16, wherein the antimicrobial agent is a tetracycline antibiotic.

* * * * *